(12) United States Patent
Hansson et al.

(10) Patent No.: US 7,766,120 B2
(45) Date of Patent: Aug. 3, 2010

(54) CAP FOR USE AS HEARING PROTECTION

(75) Inventors: Fredrik Hansson, Helsinborg (SE);
Peter Franzen, Helsinborg (SE); Per Hiselius, Lund (SE)

(73) Assignee: Sperian Hearing Protection, LLC, San Diego, CA (US)

( * ) Notice: Subject to any disclaimer, the term of this patent is extended or adjusted under 35 U.S.C. 154(b) by 862 days.

(21) Appl. No.: 11/636,248

(22) Filed: Dec. 8, 2006

(65) Prior Publication Data

US 2007/0143907 A1 Jun. 28, 2007

Related U.S. Application Data

(63) Continuation-in-part of application No. PCT/SE2005/000923, filed on Jun. 16, 2005.

(30) Foreign Application Priority Data

Jun. 16, 2004 (SE) .................................. 0401536

(51) Int. Cl.
*A42B 1/06* (2006.01)
(52) U.S. Cl. ...................... 181/129; 181/133; 181/136; 2/209; 2/423
(58) Field of Classification Search ................. 181/129, 181/133, 136; 2/209, 423
See application file for complete search history.

(56) References Cited

U.S. PATENT DOCUMENTS

| | | | | |
|---|---|---|---|---|
| 2,684,067 A * | 7/1954 | Lienard | ...................... | 128/866 |
| 3,432,861 A * | 3/1969 | Flagg | ............................. | 2/209 |
| 3,461,463 A * | 8/1969 | Beguin | ......................... | 2/423 |
| 3,579,640 A * | 5/1971 | Beguin | ......................... | 2/209 |
| 4,658,931 A | 4/1987 | Curry | | |
| 5,815,842 A * | 10/1998 | Hiselius | ......................... | 2/209 |
| 6,353,938 B1 | 3/2002 | Young | | |

FOREIGN PATENT DOCUMENTS

DE 31 19 260 A1 9/1982

* cited by examiner

*Primary Examiner*—Jeffrey Donels
*Assistant Examiner*—Jeremy Luks
(74) *Attorney, Agent, or Firm*—Leon D. Rosen

(57) ABSTRACT

The present invention relates to a cap (11) intended for use as hearing protection and adapted to enclosed the external ear of a user, characterized by at least one vibration-damping weight element (18, 38*a-b*) of the cap (11), which weight element is arranged so as to at least partly block an audio mode of vibration that would have existed in the cap in the absence of said weight element (18, 38*a-b*). The invention also relates to a method of producing such a cap, and use of the same.

14 Claims, 6 Drawing Sheets

CAP FOR USE AS HEARING PROTECTION

CROSS-REFERENCE

This is a continuation-in-part of PCT/SE2005/000923 filed 16 Jun. 2005, which claimed priority from Swedish patent application 0401536-8 filed 16 Jun. 2004.

FIELD OF THE INVENTION

The present invention relates to a cap intended for use as hearing protection and adapted to enclose the external ear of a user. The invention also relates to a method of producing such a cap, and use of such a cap.

BACKGROUND ART

A common type of hearing protection comprises two caps which are connected by a headband. The headband is adapted to be placed over the head of the user and the two caps are adapted to be arranged one on each side of the user's head so as to enclose both external ears of the user. The cap in turn comprises a cap shell, which usually is made of plastic, a sealing ring, which is adapted to fit the head of the user, and some kind of sound-absorbing material arranged inside the cap. It is also common for a so-called bottom plate to be arranged, to which the sealing ring is attached and which in turn is attached to the cap shell. Thus the bottom plate is positioned between the cap shell and the sealing ring. The bottom plate also usually acts to keep the sound absorbing material in place in the cap. As a rule, the sealing ring and bottom plate are integrated with each other, that is they are made as one unit.

The function of the hearing protection is to absorb noise from noise sources in the surroundings so that the noise does not reach the user's ears without first being dampened to acceptable levels. However, noise at certain frequencies or in certain frequency ranges may create resonance phenomena in the caps of the hearing protection, which significantly impairs the dampening of such noise.

It is known that a greater weight of the cap gives better attenuation of incoming noise, especially in the low frequency sound range, i.e. below about 1 kHz. To increase the weight of the cap, it is possible to increase the thickness of material, that is the thickness of the cap shell. Increasing the thickness "outwards" gives the drawback that the hearing protection will be larger and more unwieldy. Increasing the thickness "inwards" gives the drawback that the sound attenuation can even be impaired since the inner volume will be smaller, and a high degree of absorption requires not only weight but also a large inner volume of the cap—the relative variation in pressure of the air inside the cap will be smaller when the air volume is larger.

U.S. Pat. No. 6,353,938 B1 discloses a hearing protector with an outer cap shell of a rigid plastic material, to which a filler in the form of metal powder is added so as to increase the weight of the cap. The possibility of increasing the weight in this manner is, however, limited since there is an upper limit of how much metal can be admixed to the plastic in view of tool wear, strength properties etc. Furthermore an increase of the weight of the cap shell affects low frequency sound the most. Thus there remains the problem of damping resonance at higher frequencies, i.e. above about 1 kHz.

U.S. Pat. No. 4,658,931 discloses a hearing protector with two caps which each comprise an outer and an inner cap shell and, arranged therebetween, an evacuated cavity for attenuation of sound, which is free of transmission medium. The document mentions that a resonance frequency of one cap shell can be separated from a resonance frequency of the other cap shell by the weight of one cap shell being increased, for instance by adding extra weights inside the closed cavity. In this manner, the resonance frequency of this one cap shell is reduced, whereby the resonance frequencies of the two shells are separated. Just like in U.S. Pat. No. 6,353,938 B1, it is thus shown how sound attenuation can be improved by an increased weight of cap shells, which has the greatest effect on low frequency sound, but no solution is provided to the problem of improving sound attenuation in the higher frequency range.

SUMMARY OF THE INVENTION

An object of the present invention is to provide a cap intended for use as hearing protection, which gives improved sound attenuation as compared to prior-art hearing protection caps.

A particular object of the invention is to improve the sound attenuation of a hearing protection cap at high frequencies in the audible range, i.e. between about 1 kHz and 20 kHz.

These and other objects are achieved by the provision of a cap according to claim 1 and a method of producing such a cap according to claim 7.

The inventive cap is of the type stated by way of introduction and characterized in that the cap comprises a cap shell which supports at least one vibration-damping weight element, said weight element being arranged so as to at least partly block an audio mode of vibration that would have existed in the cap in the absence of said weight element.

By "cap" is, according to the background description above, meant the entire "unit" which is adapted to cover the user's ear and which is connected in pairs to a headband which thus joins two such units/caps. As a rule, the cap comprises a cap shell, a sealing ring, and some kind of sound-absorbing material arranged inside the cap. There is also usually a bottom plate positioned between the cap shell and the sealing ring, which plate usually keeps the sound-absorbing material in place inside the cap. As mentioned above, the bottom plate and the sealing ring can be integrated as one unit.

An "audio mode of vibration" is here defined as a "resonance peak" in a sound frequency spectrum, that is a state of, in this case, the cap in which the cap oscillates or vibrates in resonance with an incoming sound wave owing to the fact that the cap has a natural frequency at a frequency of the incoming sound wave. A cap usually has a plurality of such modes of vibration or resonance peaks along the frequency spectrum. At a frequency below about 250 Hz, the sealing ring of the cap is usually capable of producing a mode of vibration by the sealing ring acting as a resonance spring. Only at higher frequencies, above about 1 kHz, modes of vibration start to occur in the cap shell, instead of rigid body motions. In each mode of vibration above about 1 kHz, the cap shell has a certain number of vibration nodes and antinodes distributed across its surface. Vibration nodes are defined as points, lines or surfaces in an oscillating system, in which the vibrations are not noticeable, while antinodes involve the opposite, i.e. points, lines=or surfaces, in which the vibrations are at their maximum in relation to adjoining points, lines or surfaces.

Blocking an audio mode of vibration implies to change the resonance properties so that a resonance peak in the sound frequency spectrum is decreased or eliminated.

The inventive cap has several advantages over prior art hearing protection caps.

First, the inventive cap allows improved sound attenuation at high frequencies, i.e. above about 1 kHz. By carefully placing/positioning, according to the invention, weight elements in or on the cap, thereby providing selective blocking of one or more modes of vibration of the cap, the sound attenuation of the cap at high frequencies can be improved significantly. Specific blocking of at least the strongest resonance peaks in the frequency spectrum can provide good sound attenuation over the entire frequency spectrum. By arranging a plurality of weight elements in or on the cap, the attenuation can be optimized over the entire audible frequency range. At high frequencies, the location of the weight elements is more crucial to their attenuation effect than their weight.

Second, the above-mentioned problem of tool wear and reduced strength is avoided, which would otherwise occur when adding metal to the plastic of which the cap shell is made.

Third, the use of weight elements gives the advantage that the sound attenuation can be increased with retained or even reduced size/volume of the cap, especially of the cap shell. Thus, it will not be necessary to introduce the above-described problems of increased thickness of material of the cap. Thinner cap shells, which thus are made possible by the invention, result not only in lower costs of material but also in greatly shortened cooling times in the injection molding process. The cooling time is the time that dominates the production time and by shortening this, the machine cost can also be shared by more caps. Precisely the machine cost is the great cost in injection moulding. The invention thus allows lower material costs, shorter times of delivery and lower machine costs.

By the cap according to the invention comprising a cap shell which supports at least one of said weight elements, a further advantage is obtained. Especially at the higher frequencies, from about 1 kHz upwards, vibrations in the cap shell of the cap occur owing to noise from the environment. By arranging weight elements in or on the cap shell, resonances in the cap shell can be prevented from occurring. Thus, the resonances can be said to be "nipped in the bud", instead of having to be absorbed by a sound-absorbing material positioned inside the cap shell.

Preferred embodiments of the invention are defined in the dependent claims.

According to one embodiment of the present invention, effective blocking of a mode of vibration can be provided by arranging weight elements on an antinode of the cap, which antinode would have existed in the cap at said mode of vibration in the absence of said weight elements.

According to another embodiment, at least one of said weight elements has a first density and said cap shell a second density, the first density being higher than the second density. By the weight element having a higher density than the cap shell, effective resonance attenuation can be provided with a small volume of the weight element. Thus, the inner volume of the cap which is required for absorption is not used to a very great extent.

In yet another embodiment, at least one of said weight elements is attached to the cap shell by said weight element being at least partly moulded into the cap shell. Attaching weight elements by moulding allows exact positioning of the weight element and stable fixation of the same.

In a further embodiment of the invention, the cap comprises a bottom plate which carries at least one of said weight elements. In some cases, it is advantageous to block resonance vibrations by arranging weight elements on or in the bottom plate of the cap. Such cases may exist, for instance, when the bottom plate itself comes into resonance vibration or, since the cap parts are connected to each other, when it is difficult to block a certain mode of vibration of the cap shell by arranging weight elements on the cap shell, but this mode of vibration can be blocked by arranging weight elements on or in the bottom plate.

In yet another embodiment, at least one of said weight elements has a density which is higher than a density of the bottom plate. In the same way as stated above concerning the cap shell, a higher density of the weight element than that of the bottom plate on or in which it is arranged, provides effective resonance attenuation with a small volume of the weight element.

According to another aspect of the present invention, a method of producing a cap intended for use as hearing protection is characterised by the steps of supplying a cap designed to enclose a user's external ear, and arranging at least one vibration-damping weight element in or on the cap in such a manner that the weight element at least partly blocks an audio mode of vibration that would have existed in the cap in the absence of the weight element, the step of arranging said weight element in or on the cap comprising the step of arranging the weight element in or on a cap shell of the cap. In the same way as the inventive cap described above, this inventive method of producing a cap for hearing protection gives a plurality of advantages as compared to prior-art methods of producing hearing protection caps. As mentioned above, the use of weight elements gives the advantage that sound attenuation can be increased without changing the volume of the cap, which means that it is-not necessary to introduce the problems of increased thickness of material of the cap. The problems of tool wear and reduced strength are avoided, which would otherwise occur when adding metal to the plastic of which the cap shell is made. Furthermore the-inventive method of producing a cap allows improved sound attenuation at high frequencies, i.e. above about 1 kHz, by the weight element being arranged in the cap in such a manner that audio modes of vibration are blocked.

Preferred embodiments of the inventive method of producing a cap are evident from the dependent claims. These embodiments of the method of producing the cap allow the same advantages as corresponding embodiments of the inventive cap.

BRIEF DESCRIPTION OF THE DRAWINGS

The invention will now be described in more detail with reference to the accompanying schematic drawings, in which.

DESCRIPTION OF THE PREFERRED EMBODIMENTS

Figure 1:
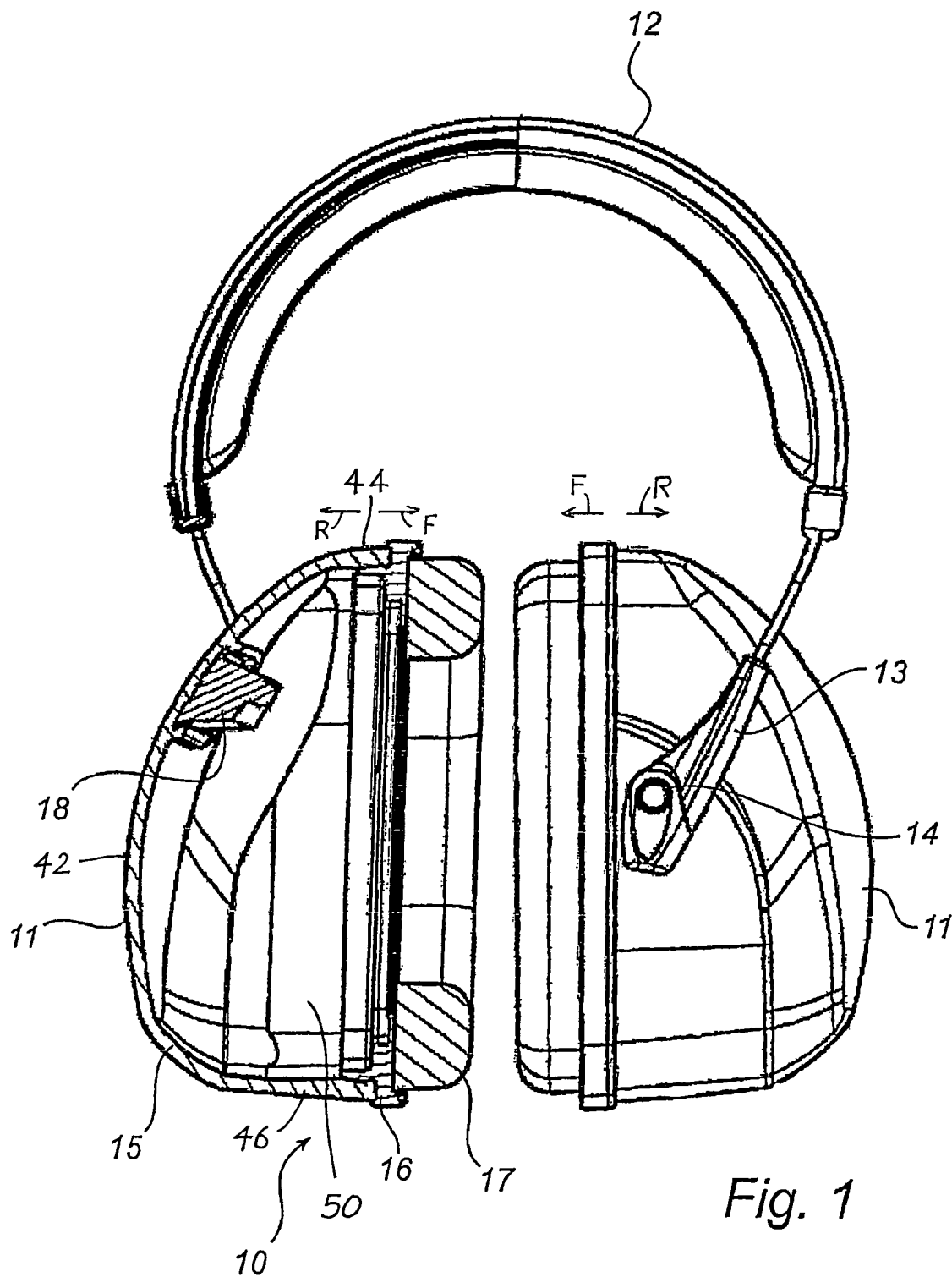
FIG. 1 is a top plan view of a hearing protector whose left half is shown in cross-section, with an embodiment of caps according to the present invention.

FIG. 1 illustrates a hearing protector 10 comprising a headband 12 to abut against a user's crown and an embodiment of a cap 11 according to the invention to be mounted at each end of the headband, thus enclosing an external ear of the user. Each cap 11 comprises a cap shell 15, an intermediate bottom plate 16 and a sealing ring 17 to seal against the head of the user. A sound absorbing material (not shown) is preferably arranged between the cap shell 15 and the bottom plate 16, for instance in the form of a pad of foam plastic. Each cap is mounted at an end of the headband 12 by suspension from pins 14 on opposite sides of the cap shell 15, which pins are inserted into corresponding holes of holders 13 at each end of the headband 12, so that the caps 11 are pivotally suspended from the headband 12.

Each cap has front F and rear R ends that lie respectively closest and furthest from the person's ear. Each cap shell 15 has a closed rear wall 42, closed top and bottom walls 44, 46, and closed opposite side walls 50. The top, bottom, and side walls all merge with the rear wall. The cap shell is molded of a polymer that has a density of no more than 2 (water has a density of 1.0) and with a density that is usually no more than 1.5.

According to the present invention, each cap 11 further comprises a vibration-absorbing weight element 18 which is positioned so as to at least partly block an audio mode of vibration which would have existed in the cap in the absence of said weight element. According to the definition above, an audio mode of vibration is a resonance peak in a sound frequency spectrum, that is a state of the cap in which the cap oscillates or vibrates in resonance with an incoming sound wave. Blocking an audio mode of vibration implies, as stated above, to reduce or eliminate a resonance peak in the sound frequency spectrum.

In the embodiment shown in FIG. 1, the weight element 18 is positioned by being attached to the rear wall of the cap shell 15. Especially at the higher frequencies, from about 1 kHz upwards, vibrations occur in precisely the cap shell of the cap due to noise from the environment. By arranging the weight element 18 in the cap shell 15, resonances in the cap shell 15 can be prevented from occurring at certain frequencies of the incoming sound.

The weight element 18 preferably has a density which is higher than the density of the cap shell 15 as such. As a result, effective resonance absorption can be provided with a relatively small volume of the weight element 18. The difference in density can be provided by the weight element 18 being made of a heavy material, such as metal, preferably zinc (density of 7.1) or a zinc alloy, while the cap shell 15 is in a conventional way made of plastic (density no more than 2 and usually no more than 1.5). Zinc has like several other metals, such as iron (density of 7.9), a significantly higher density than plastic (in the order of seven times higher). In addition zinc is relatively easy to form to the desired shape.

The weight element 18 has a density more than twice that of the plastic of the cap shell, and usually at least four times that of the plastic of the cap shell. To have a significant effect on resonance absorption, the weight member has a mass or weight) of at least 5% of the shell mass.

The weight element 18 is formed to fit the cap shell 15. Forming of the weight element 18 can occur, for instance, by die casting, punching, forging, turning, milling, drilling or die stamping, in which complex shapes for continued production can be achieved.

Figure 2:
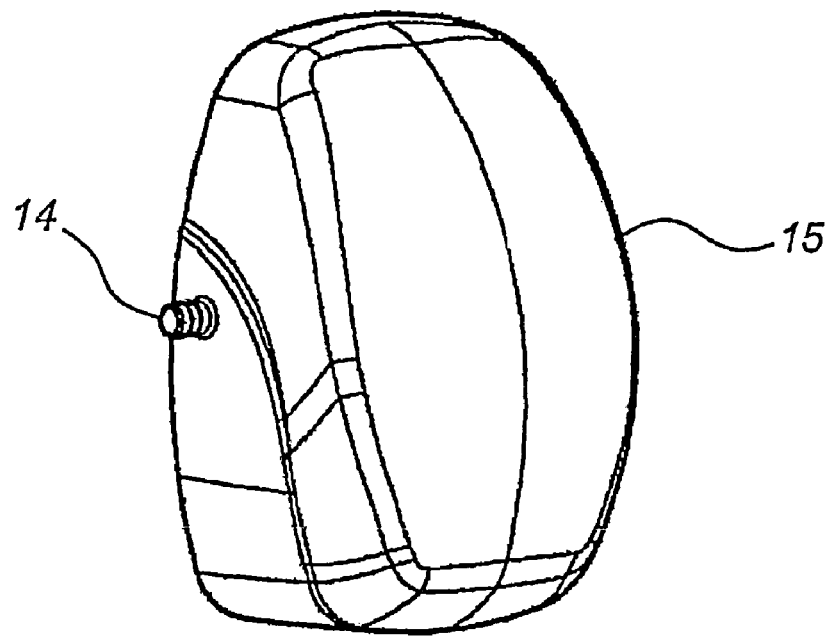
FIGS. 2 and 3 are two different perspective views of a cap shell of a cap according to FIG. 1.
Figure 3:
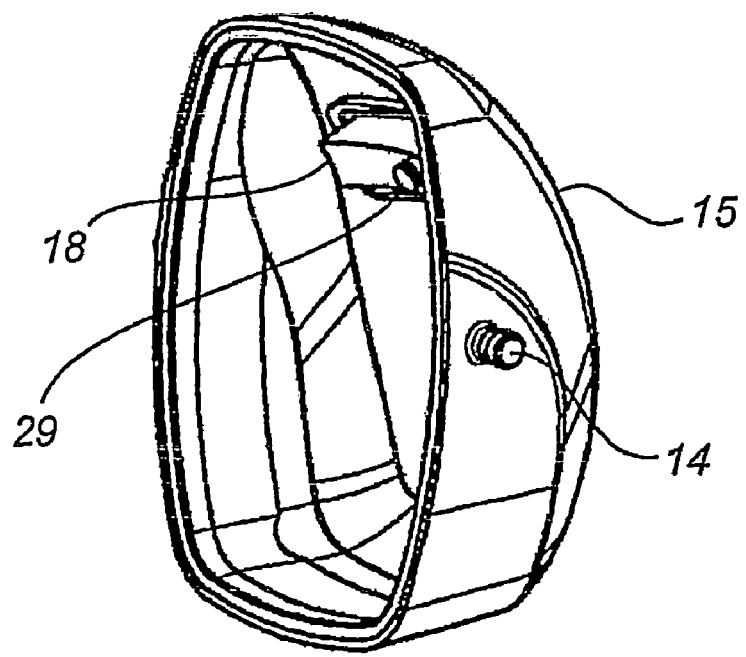

FIGS. 2 and 3 show from different directions merely the cap shell 15 with the suspension pin 14 and the weight element 18. As is evident from FIG. 2, the weight element 18 is not visible from the outside of the cap shell 15.

In an alternative embodiment, the cap shell could be made of a wholly or partly transparent material, such as transparent plastic, which would make it possible to show, for instance, a decoration, an emblem, a logotype of a company, color coding or some other information which is attached to the inside of the cap shell and, thus, is protected from outer wear on the cap shell. A weight element according to the invention could constitute such an emblem, for instance in the form of a logotype of a company, and thus be visible through the cap shell. The transparent cap shell means, in this case, also extra safety for the user since he can control that the vibration-damping weight elements are properly attached inside the cap shell.

Figure 4:
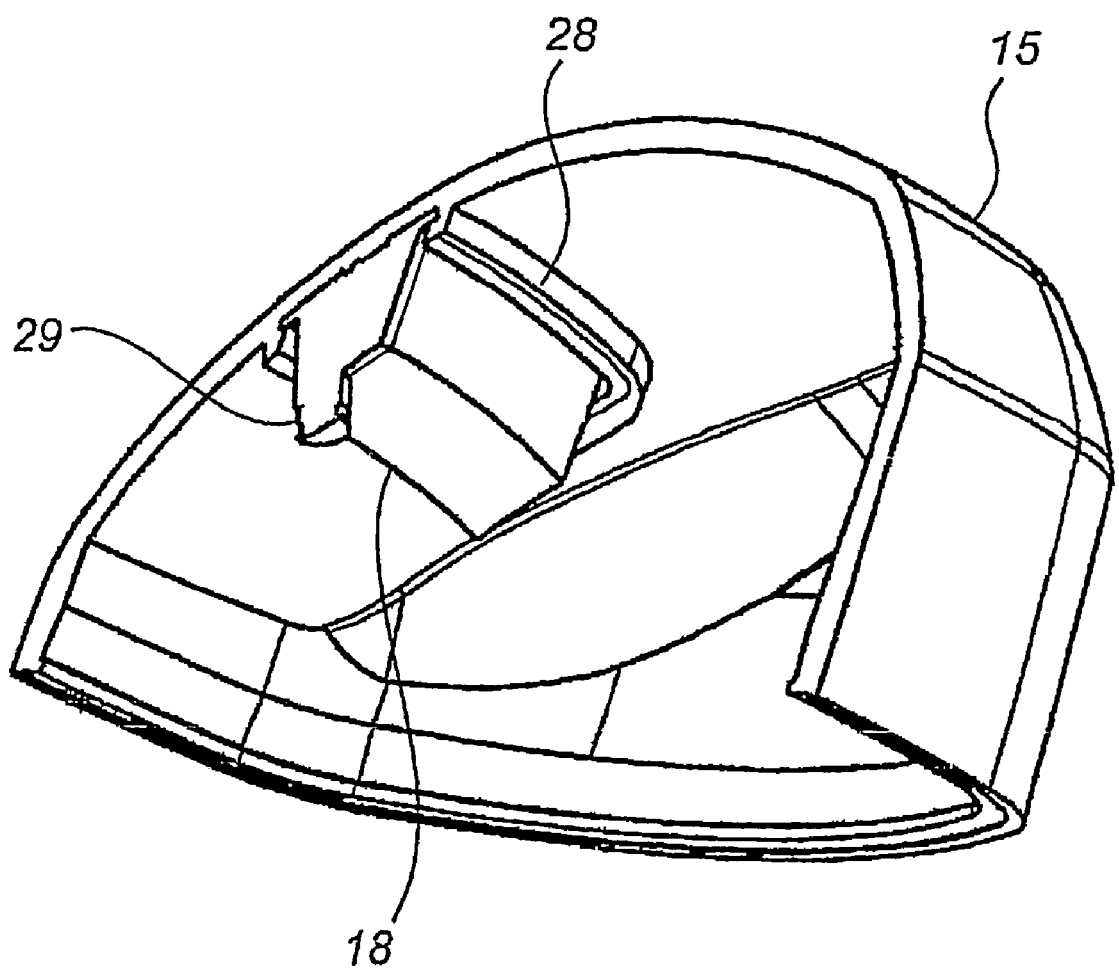
FIG. 4 is a cross-section of the cap shell according to FIGS. 2 and 3 in perspective.

FIG. 3 also shows a pin 29 which is a rest from the production of the cap shell 15 comprising the weight element 18. The pin 29 is also shown in cross-section in FIG. 4, from which it is also distinctly to be seen how the weight element 18 is partly molded into the cap shell 15 in such a manner that a projecting rim portion of the weight element 18 is surrounded by a superposed edge 28 molded integrally with the cap shell 15 as such. By the weight element 18 thus by molding being attached to the cap shell 15, exact positioning of the weight element 18 and reliable fixing of the same are allowed.

Figure 5:
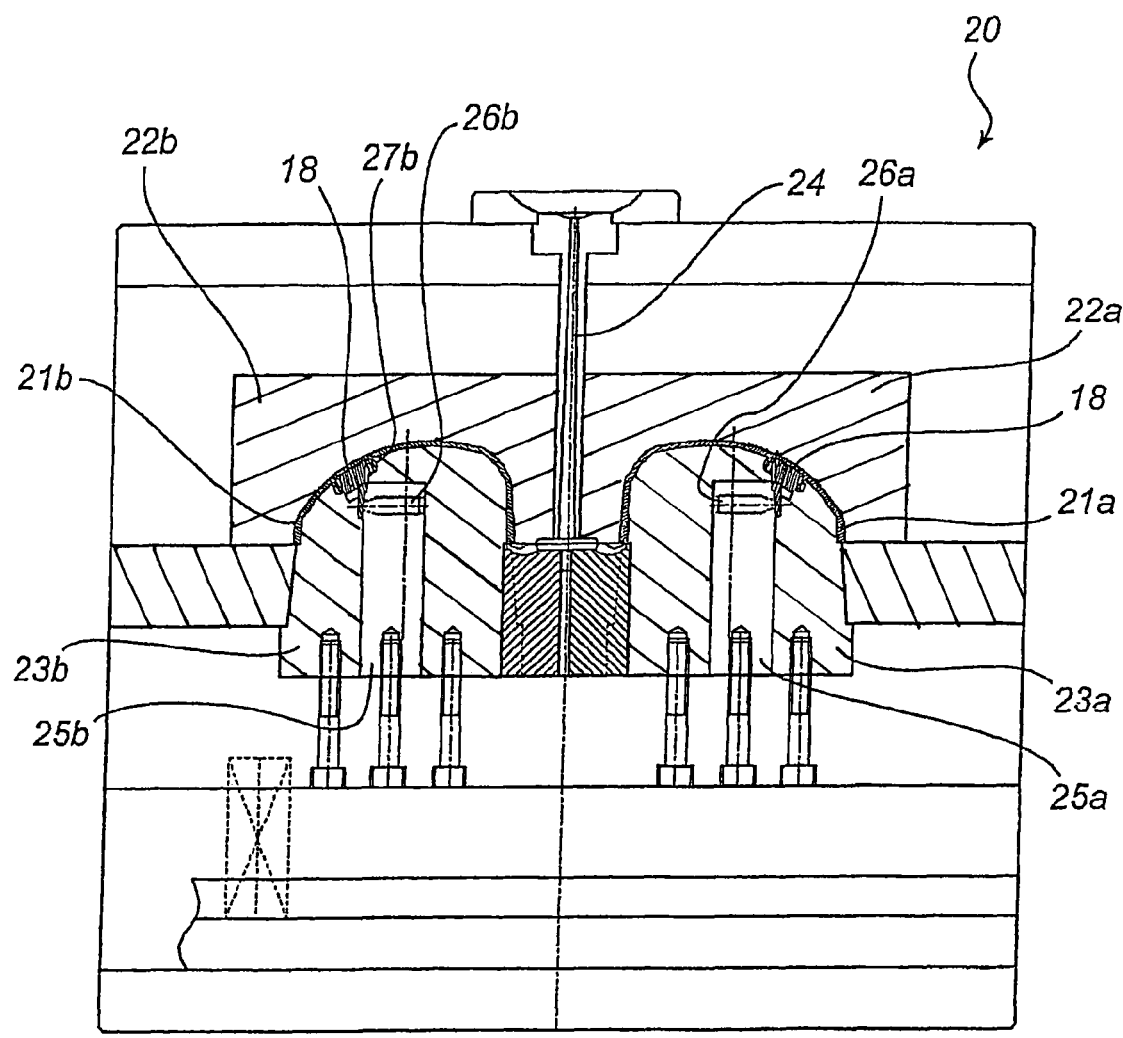
FIG. 5 is a cross-section of an injection mold intended for simultaneous production of two cap shells according to FIGS. 1-4.

FIG. 5 illustrates in cross-section an injection mold for producing a cap shell 15 of plastic with a weight element 18 of metal attached thereto. The injection mold comprises a mold 20 which defines two cavities 21a-b to which plastic is adapted to be supplied to form two cap shells 15. The boundary surfaces of the cavities 21a-b are formed by outer molds 22a-b and inner molds 23a-b. The plastic is supplied through a runner 24 to the interior of the mold 20 and to the two cavities 21a-b. For the plastic to fill the cavities 21a-b completely, it is supplied in a heated, moldable state under pressure. The selection of pressure and temperature depends on, inter alia, what type of polymer material is used and how complicated a shape the object to be injection molded has. Moreover the shape and the necessary pressure will control if, and in that case, in what directions and along what parting lines it is convenient to divide the outer mold and/or inner mold into a plurality of parts. Injection molding of polymer material is a commercially well-known technique, and since the decisions just mentioned are obvious to a person skilled in the art, only one alternative will be described and only at a-level of details that is necessary for the understanding of the invention.

FIG. 5 shows how the inner molds 23a-b have been adjusted so that they each comprise a specially designed inner part 25a-b which in turn comprises a holder 26a-b. The holder 26a-b is arranged to keep a weight element 18 in the correct position of the cavity 21a-b so that the weight element 18 is partly molded into the cap shell 4a-b when the plastic is supplied to the cavity 21a-b through said runner 24. The inner molds 23a-b are further formed with an annular recess 27a-b which extends around each of said weight elements 18. The recesses 27a-b will be filled with plastic and the cap shell 15 will thus be formed with an edge 28 extending around each of said weight elements 18. The weight element 18 is provided with a pin 29 which said holder 26a-b is arranged to engage to keep the weight element 18 in place in the cavities 21a-b.

Some other ways than precisely injection molding for securing weight elements to a cap will be described below.

Gluing or using adhesive tape: Weight elements can be glued to a part of the cap, such as the cap shell, using different types of glue or adhesive according to the properties of the materials of which the cap part and the weight element are made. The components can also be joined by tape.

Joining by heat: A hot weight element of, for instance, metal can be pressed into a cap part made of plastic.

Riveting or screwing: The cap part can be riveted or screwed to the weight element, or vice versa.

FIGS. 1-5 illustrate how a weight element can be, mounted on the inside of the rear wall of a cap shell. The weight element can, however, also be arranged on the outside of the cap shell, or in or on the bottom plate 16 which can be integrated with the sealing ring 17 (see FIG. 1). As mentioned above, it may in some cases be advantageous to block resonance vibrations by arranging weight elements in or on the bottom plate of the cap, for instance when the bottom plate itself comes into resonance vibration or when it is difficult to block a certain mode of vibration of the cap shell by arranging weight elements on the cap shell, but blocking of this mode of vibration can be provided with a weight element in/on the bottom plate.

Preferably, also weight elements arranged in or on the bottom plate have a density which is higher than the density of the rest of the bottom plate, plus optionally the sealing ring. In the same way as stated above regarding the cap shell, a higher density of the weight element than that of the bottom plate results in effective resonance absorption with a small volume of the weight element.

To find out where in or on the cap weight elements are to be arranged so as to provide blocking of one or more modes of vibration, it is possible to use two fundamentally different methods, which will be exemplified below:

testing where weight elements are to be arranged, or first analyzing where in the cap antinodes occur for one or more modes of vibrations and then arranging weight elements on these antinodes.

In both methods, it is necessary to measure in some way the sound attenuation effect that is achieved when arranging weight elements in/on the cap in relation to the sound attenuation effect achieved without weight elements. There are different ways of doing this. One way is to measure, with microphones arranged in the ears of an individual or on an artificial head, the sound volume at different frequencies along the audible frequency spectrum from a loudspeaker in the neighbourhood, first completely without a hearing protector, as a reference, and then with a hearing protector arranged on the head above the microphones. In the first measurement, the hearing protector is without weight elements. By means of a computer program, the attenuation which is provided with the hearing protector is then calculated, in relation to without the hearing protector, by comparing, for the various frequencies, the sound volume measured without a hearing protector, with the sound volume measured with a hearing protector. By frequency analysis of the attenuation, an attenuation spectrum is obtained, in which it is possible to see at what frequencies the attenuation is insufficient, which most probably depends on the fact that at these frequencies resonances or modes of vibration occur in the caps of the hearing protector. Subsequently, the measuring process is repeated with and without the hearing protector, but this time the caps of the hearing protector are fitted with weight elements. By comparing the attenuation spectra for a hearing protector with and without weight elements, it is possible to see whether one or more modes of vibrations could be blocked by means of the weight element or weight elements.

Testing where weight elements are to be arranged can be performed in the following way:

1. Measuring an attenuation spectrum for a cap with out weight elements;
2. Arranging a weight element in or on the cap;
3. Measuring the attenuation spectrum for the cap with the weight element mounted. Has a sufficient number of modes of vibrations been blocked? If not, repeat steps 1-3, the weight element being arranged somewhere else or a plurality of weight elements being arranged in or on the cap.

Figure 6:
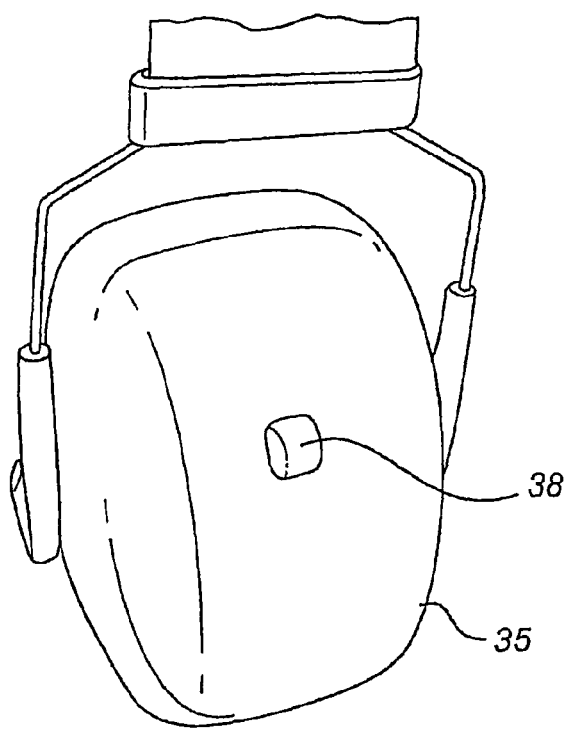
FIG. 6 is a schematic view of another embodiment of a cap according to the invention.
Figure 7:
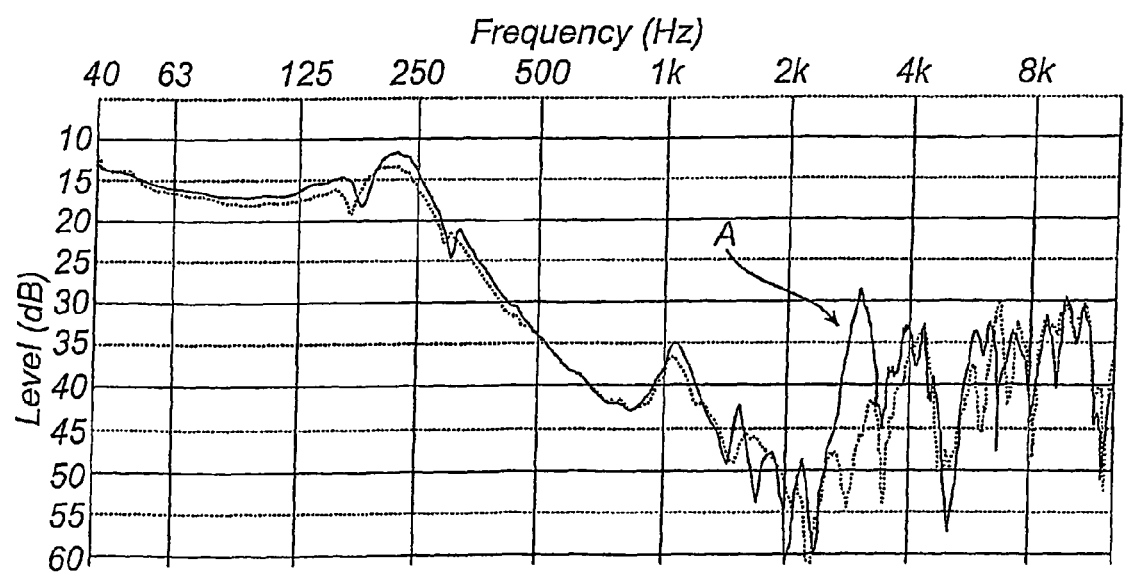
FIG. 7 illustrates an attenuation spectrum for the cap according to FIG. 6.

FIG. 6 illustrates a cap, on which a weight element 38 weighing about 10 g is arranged in the centre of the cap shell 35. FIG. 7 shows an attenuation spectrum measured according to that stated above, in which the result of the arrangement of the weight element 38 can be seen. In the spectrum, the solid curve indicates the attenuation in the cap without the weight element 38, while the dashed line indicates the attenuation with the weight element 38 mounted. As can be seen from the spectrum, the mode of vibration A is blocked at about 3 kHz by the weight element 38. It is distinctly to be seen from the attenuation spectrum that the cap has a plurality of modes of vibration along the frequency range and that these modes are positioned substantially more closely to each other above about 1 kHz. This is due to the fact that modes of vibration of the cap shell itself, implying that the cap shell does not move as a rigid body but instead oscillates in inner wave motions, in most cases start precisely at about 1 kHz.

Figure 8:
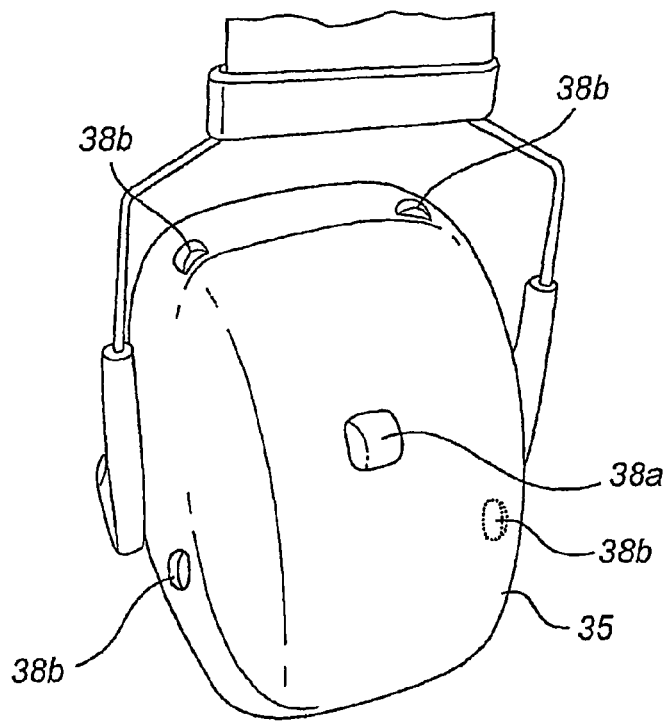
FIG. 8 is a schematic view of another embodiment of a cap according to the invention.

FIG. 8 illustrates a cap similar to the one in FIG. 6, although with a plurality of weight elements 38a and 38b arranged on the cap shell 35. The weight element 38a which is arranged in the center of the cap shell 35, weighs about 10 g, while the other weight elements 38b weigh about 5 g.

Figure 9:
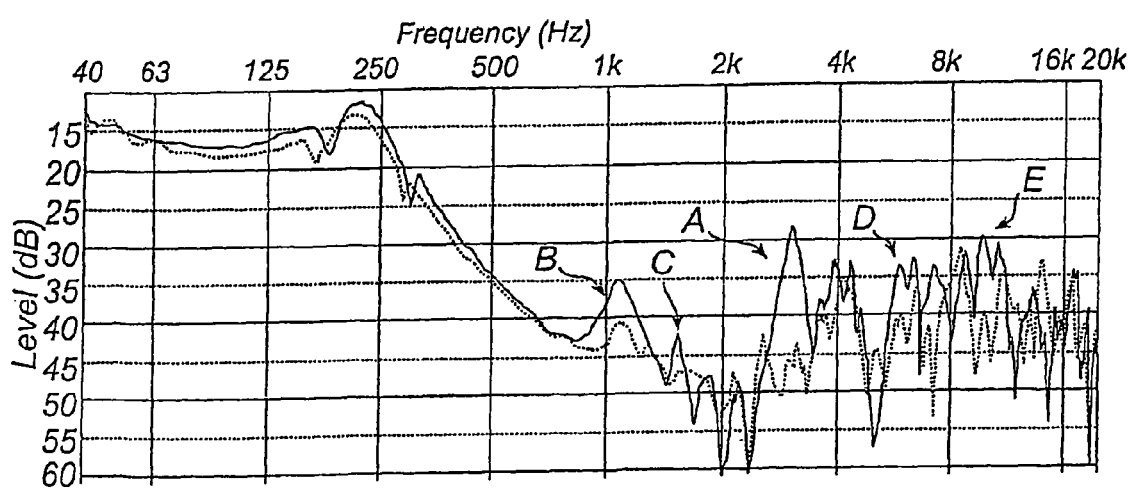
FIG. 9 illustrates an attenuation spectrum for the cap according to FIG. 8.

FIG. 9 shows the result of the arrangement according to FIG. 8 in an attenuation spectrum. As can be seen from the Figure, not only the mode of vibration A has been blocked, but also additional modes of vibration B, C, D and E have been blocked. Applicant considers a node significant where noise attenuation without a weight member is at least 3 dB less than at frequencies that lie above and below the node and that have a slope (of the attenuation-frequency curve) of zero (e.g. for node B of 1.1 KHz the frequencies of zero slope on opposite sides of B are at 900 Hz and 1.25 Hz).

Another method of finding out where in and on the cap weight elements are to be arranged involves, as mentioned above, first analyzing where in the cap antinodes occur and then arranging weight elements on these antinodes. The result of the arrangement can in the same way as stated above be evaluated by preparing attenuation spectra.

Such an analysis of where antinodes occur can be made by a so-called modal analysis, for example, by finite element calculations or by vibration measurements, for instance by means of laser. These different ways of making a modal analysis are well known to those skilled in the art in the field of acoustics, and therefore a description of examples of the use of such methods for the above-mentioned purpose is not necessary for the understanding of the invention and will therefore not be given here.

Arranging a weight element in the center of an antinode of the cap, which antinode occurs at a certain mode of vibration, blocks in most cases not just the current mode of vibration but also other modes of vibration, whose antinodes coincide with the antinode of the current mode of vibration. A cap usually has, which is evident from FIGS. 7 and 9, a plurality of modes of vibration or resonance peaks along the frequency spectrum. In each such mode of vibration, the cap has a predetermined number of vibration nodes and antinodes distributed over, for instance, the surface of the cap shell.

This method of first finding out where the antinodes are located and then arranging weight elements on them, can be used in the cases where the previously described testing process has failed or where, for some other reason, it is desirable to make it easier to effectively prevent such modes of vibration. For instance, if a weight element is to be molded into the cap shell, it is particularly important for the location of the weight element to be correct since the cost of making a new mold would be too great.

It will be appreciated that modifications of the systems and methods described above can be made by a person skilled in the art without deviating from the spirit and scope of the invention.

What is claimed is:

1. A cap intended for use as hearing protection and adapted to enclose a user's external ear, characterized in that:
the cap (11) comprises a cap shell (15; 35) which supports at least one vibration-damping weight element (18; 38a-b), said weight element being arranged so as to at least partly block an audio mode of vibration that would have existed in the cap (11) in the absence of said weight element (18; 38a-b), wherein said at least one vibration-damping element (18; 38a-b) is placed on an antinode of the cap (11), which antinode would have existed in the cap in said mode of vibration in the absence of said weight element (18; 38a-b).

2. A cap as claimed in claim 1, wherein at least one of said weight elements (18; 38a-b) has a first density and said cap shell (15; 35) has a second density, the first density being higher than the second density.

3. A cap as claimed in claim 1 or 2, wherein at least one of said weight elements (18; 38a-b) is attached to the cap shell (15; 35) by said weight element (18; 38a-b) being at least partly molded into the cap shell (15; 35).

4. A cap as claimed in claim 1, which cap (11) further comprises a bottom plate (16) which carries at least one of said weight elements (18; 38a-b).

5. A cap as claimed in claim 4, wherein at least one of said weight elements (18; 38a-b) has a density which is higher than a density of the bottom plate (16).

6. A method of producing a cap intended for use as hearing protection, characterised by the steps of forming a cap (11) having a shell with inside and outside surfaces and designed to enclose most of a user's external ear, comprising:
arranging at least one vibration-damping weight element (18; 38a-b) on the cap (11) in such a manner that the weight element (18; 38a-b) at least partly blocks an audio mode of vibration that would have existed in the cap (11) in the absence of the weight element (18; 38a-b), the step of arranging said weight element (18; 38a-b) on the cap (11) comprising the step of arranging the weight element (18; 38a-b) on one of said surfaces of said cap shell (15; 35), wherein the step of arranging said weight element (18; 38a-b) on the cap (11) comprises the step of placing the weight element (18; 38a-b) on an antinode of the cap (11), which antinode would have existed in the cap (11) in said mode of vibration in the absence of the weight element (18; 38a-b).

7. A method as claimed in claim 6, further comprising the step of giving at least one of said weight elements (18; 38a-b) a first density and said cap shell (15; 35) a second density, the first density being higher than the second density.

8. A method as claimed in claim 6 or 7, wherein the step of arranging said weight element (18; 38a-b) in or on the cap (11) further comprises the step of securing at least one of said weight elements (18; 38a-b) to the cap shell (15; 35) by at least partly molding said weight element (18; 38a-b) into the cap shell (15; 35).

9. A method as claimed in claim 6, wherein the step of arranging said weight element (18; 38a-b) on the cap (11) comprises the step of arranging the weight element (18; 38a-b) on a bottom plate (16) of the cap (11).

10. A method as claimed in claim 9, further comprising the step of giving at least one of said weight elements (18; 38a-b) a density which is higher than a density of the bottom plate (16).

11. A hearing protector for hearing protection, which includes a first cap that lies against an ear of a person, wherein said first cap includes a shell with a closed rear wall that is furthest from the person's ear and an open front and an elastic seal ring that extends around said open front, wherein:
said first cap includes a first shell that is formed of polymer material having a density of no more than 2;
said first cap also includes a discrete weight member of material at least twice as dense as the material of said first shell, said discrete weight member being fixed to a location on said first shell, wherein said location where said discrete weight member is fixed to said first shell is a location where a sound wave node occurs at a predetermined sound frequency of at least one KHz when the weight member is not fixed to said location.

12. The hearing protector described in claim 11 wherein:
said weight member has a weight of at least 5% of the weight of said shell.

13. The hearing protector described in claim 11 wherein said shell includes closed opposite sides, a closed top, and closed bottom, that each has inside and outside surfaces and that each merges with said first shell rear wall, wherein:
said weight member is attached to said first shell rear wall.

14. The hearing protector described in claim 13 wherein:
said weight member is attached to a middle of said first shell rear wall.

* * * * *